United States Patent
Moses et al.

(10) Patent No.: US 9,585,744 B2
(45) Date of Patent: Mar. 7, 2017

(54) SYSTEMS AND METHODS FOR MASTOPEXY

(71) Applicant: Tepha, Inc., Lexington, MA (US)

(72) Inventors: Arikha Moses, New York, NY (US); Emily Stires, Boston, MA (US); Anthony Natale, New Preston, CT (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 14/830,685

(22) Filed: Aug. 19, 2015

(65) Prior Publication Data

US 2015/0351891 A1    Dec. 10, 2015

Related U.S. Application Data

(63) Continuation of application No. 14/249,155, filed on Apr. 9, 2014, now Pat. No. 9,277,986, which is a continuation of application No. 13/413,770, filed on Mar. 7, 2012, now Pat. No. 8,858,629.

(60) Provisional application No. 61/451,103, filed on Mar. 9, 2011, provisional application No. 61/604,242, filed on Feb. 28, 2012.

(51) Int. Cl.
    *A61F 2/12*  (2006.01)
    *A61L 31/14* (2006.01)
    *A61F 2/00*  (2006.01)

(52) U.S. Cl.
    CPC ............. *A61F 2/12* (2013.01); *A61F 2/0063* (2013.01); *A61L 31/148* (2013.01); *A61F 2002/0068* (2013.01); *A61F 2002/0072* (2013.01); *A61F 2220/0008* (2013.01); *A61F 2230/001* (2013.01); *A61F 2230/0013* (2013.01);

(Continued)

(58) Field of Classification Search
    CPC ................................ A61F 2/12; A61F 2/0063
    USPC ......................................................... 623/7-8
    See application file for complete search history.

(56) References Cited

U.S. PATENT DOCUMENTS 4,372,293 A   2/1983   Vijil-Rosales
5,217,494 A   6/1993   Coggins
(Continued)

FOREIGN PATENT DOCUMENTS

WO   2004/096098   11/2004
WO   2006/117622   11/2006
(Continued)

OTHER PUBLICATIONS

WrtnOpn of ISR issued Nov. 5, 2012 for PCT/US2012/027975.
(Continued)

*Primary Examiner* — Suzette J Gherbi
(74) *Attorney, Agent, or Firm* — Convergent Law Group LLP; Rick Batt

(57) ABSTRACT

A mastopexy implant for maintaining the breast in an elevated and aesthetically pleasing position includes a lower pole support comprising end portions which may be affixed to the chest wall or to a previously installed upper suspension strut. The implant is loaded in an insertion device. The insertion device is inserted through a small incision and into a subcutaneous pocket created in an inferior half of the breast. The lower pole support may have various constructs and in one embodiment includes a unitary conformable mesh having a plurality of arm or band members which are attached across the breast parenchyma and to the chest wall.

23 Claims, 12 Drawing Sheets

(52) U.S. Cl.
CPC ............... *A61F 2230/0058* (2013.01); *A61F 2230/0076* (2013.01)

(56) References Cited

U.S. PATENT DOCUMENTS

| | | | |
|---|---|---|---|
| 5,356,429 | A | 10/1994 | Seare |
| 5,500,019 | A | 3/1996 | Johnson |
| 5,545,221 | A | 8/1996 | Hang-Fu |
| 5,584,884 | A | 12/1996 | Pignataro |
| 5,658,328 | A | 8/1997 | Johnson |
| 5,676,161 | A | 10/1997 | Breiner |
| 5,716,404 | A | 2/1998 | Vacanti |
| 5,759,204 | A | 6/1998 | Seare |
| 5,990,378 | A | 11/1999 | Ellis |
| 6,210,439 | B1 | 4/2001 | Firmin |
| 6,328,765 | B1 | 12/2001 | Hardwick |
| 6,368,541 | B1 | 4/2002 | Pajotin |
| 6,599,323 | B2 | 7/2003 | Melican |
| 6,723,133 | B1 | 4/2004 | Pajotin |
| 6,740,122 | B1 | 5/2004 | Pajotin |
| 6,913,626 | B2 | 7/2005 | McGhan |
| 7,081,135 | B2 | 7/2006 | Smith |
| 7,476,249 | B2 | 1/2009 | Frank |
| 7,670,372 | B2 | 3/2010 | Shfaram |
| 7,875,074 | B2 | 1/2011 | Chen |
| 8,007,531 | B2 | 8/2011 | Frank |
| 8,034,270 | B2 | 10/2011 | Martin |
| 8,728,159 | B2 * | 5/2014 | Kim ............... A61F 2/12 623/8 |
| 8,858,629 | B2 * | 10/2014 | Moses ............ A61F 2/12 623/8 |
| 8,986,377 | B2 | 3/2015 | Richter |
| 9,277,986 | B2 * | 3/2016 | Moses ............ A61F 2/12 |
| 2003/0207649 | A1 | 11/2003 | Reeder |
| 2006/0167338 | A1 | 7/2006 | Shfaram |
| 2006/0211334 | A1 | 9/2006 | Smith |
| 2007/0135929 | A1 * | 6/2007 | Williams .......... A61F 2/07 623/23.75 |
| 2008/0027273 | A1 | 1/2008 | Gutterman |
| 2008/0082113 | A1 | 4/2008 | Bishop |
| 2008/0097601 | A1 | 4/2008 | Codori-Huff |
| 2009/0082864 | A1 | 3/2009 | Chen |
| 2009/0240342 | A1 | 9/2009 | Lindh |
| 2009/0248071 | A1 * | 10/2009 | Saint ............... A61B 17/0401 606/232 |
| 2010/0191330 | A1 | 7/2010 | Lauryssen |
| 2010/0204791 | A1 | 8/2010 | Shfaram |
| 2010/0217388 | A1 | 8/2010 | Cohen |
| 2010/0331612 | A1 | 12/2010 | Lashinski |
| 2011/0009960 | A1 * | 1/2011 | Altman ............ A61F 2/0059 623/8 |
| 2011/0022171 | A1 | 1/2011 | Richter |
| 2011/0257665 | A1 | 10/2011 | Mortarino |
| 2012/0004723 | A1 * | 1/2012 | Mortarino ........ A61F 2/0063 623/8 |
| 2012/0022646 | A1 * | 1/2012 | Mortarino ........ A61L 27/3604 623/8 |
| 2012/0158134 | A1 * | 6/2012 | Codori-Hurff .... A61F 2/12 623/8 |
| 2012/0185041 | A1 | 7/2012 | Mortarino |
| 2012/0221105 | A1 * | 8/2012 | Altman ............ A61F 2/08 623/8 |
| 2012/0232653 | A1 * | 9/2012 | Saint ............... A61B 17/0401 623/8 |
| 2012/0283826 | A1 | 11/2012 | Moses |
| 2013/0066423 | A1 * | 3/2013 | Bishop ............ A61B 17/06166 623/8 |
| 2013/0103149 | A1 * | 4/2013 | Altman ............ A61F 2/0059 623/8 |
| 2013/0178699 | A1 * | 7/2013 | Saint ............... A61B 17/0401 600/37 |
| 2013/0178875 | A1 | 7/2013 | Horton |
| 2013/0253645 | A1 | 9/2013 | Kerr |
| 2013/0304098 | A1 | 11/2013 | Mortarino |
| 2014/0200396 | A1 | 7/2014 | Lashinski |
| 2014/0222146 | A1 | 8/2014 | Moses |
| 2014/0222161 | A1 | 8/2014 | Mathisen |
| 2014/0276997 | A1 | 9/2014 | Harrah |
| 2015/0012089 | A1 | 1/2015 | Shetty |
| 2015/0018946 | A1 | 1/2015 | Guterman |
| 2015/0056131 | A1 | 2/2015 | Bernasconi |
| 2015/0223928 | A1 | 8/2015 | Limem |
| 2015/0351899 | A1 | 12/2015 | Mortarino |
| 2016/0022416 | A1 * | 1/2016 | Felix ............... B29C 47/08 623/8 |
| 2016/0038269 | A1 | 2/2016 | Altman |
| 2016/0151138 | A1 | 6/2016 | Guterman |

FOREIGN PATENT DOCUMENTS

| | | |
|---|---|---|
| WO | 2009/001293 | 12/2008 |
| WO | 2009050706 | 4/2009 |
| WO | 2011/119742 | 9/2011 |
| WO | 2012/122215 | 9/2012 |
| WO | 2015006737 | 1/2015 |

OTHER PUBLICATIONS

GalaFLEX Mesh . . . Supporting Your Quest for Timeless Beauty, Tepha, Inc., 400109 Rev.B, Oct. 2012.

GalaFLEX Mesh, TEPHA, Inc., www.galateasurgical.com, P/N. 400124, Rev. A, Oct. 2013.

Supplementary European Search Report of the EPO issued Jul. 30, 2014, EP 12754773.5 from PCT/US2012/027075.

Auclair, et al, "Repair of mammary ptosis by insertion of an internal absorbable support and periareaolar scar," Ann Chir Plast Esthet, 1993, 38, No. 1, pp. 107-113.

DeBruijn, et al, "Mastopexy with Mesh Reinforcement: The Mechanical Characteristics of Polyester Mesh in the Female Breast," Plast. Reconstr. Surg. 124: 364, 2009.

Goes, "Periareolar mammaplasty: double skin technique with application of polyglactine or mixed mesh," Plast. Reconstr. Surg., 97-859-68 (1996).

Goes, "Periareolar Mastopexy with FortaPerm," Aesth. Plast. Surg., 34-350-8, 2010.

Goes, "Periareolar mammaplasty: double-skin technique with application of mesh support," Clin Plastic Surg 29 (2002) 349-364.

Johnson, "Central core reduction mammoplasties and Marlex suspension of breast tissue,".

P. van Deventer, Improving the Longevity and Results of Mastopexy and Breast Reduction Procedures: Reconstructing an Internal Breast Support System with Biocompatible Mesh to Replace the Supporting Function of the Ligamentous Suspension, Aesth Plast Surg (2012) 36:578-589, DOI 10.1007/s00266-011-9845-2.

Williams, "Poly-4-hydroxputyrate (P4HB): a new generation of resorbable medical devices for tissue repair and regeneration," DOI 10.1515/bmt-2013-0009 Biomed Tech 2013; 58(5): 439-452.

* cited by examiner

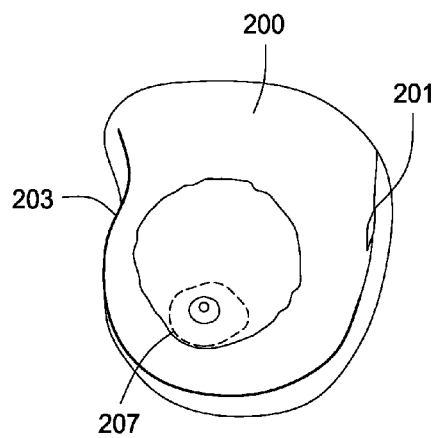
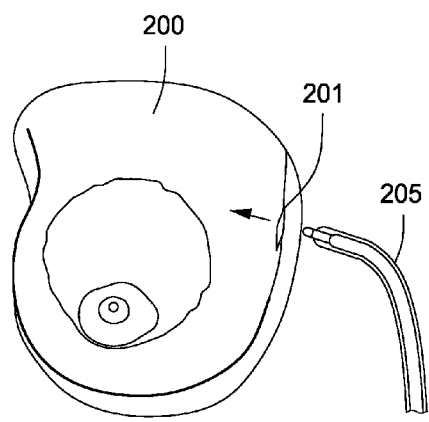
FIG. 2A    FIG. 2B
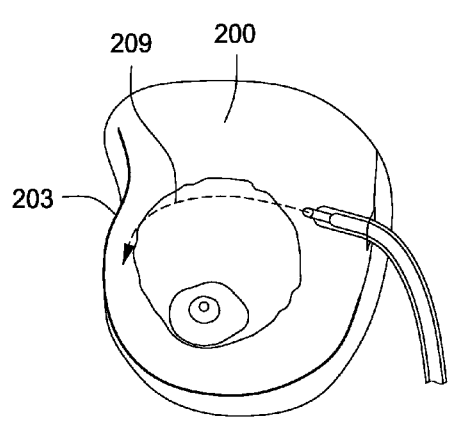
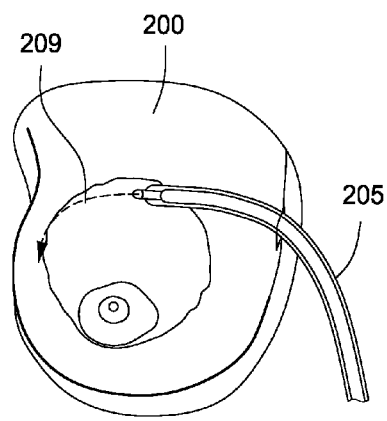
FIG. 2C    FIG. 2D

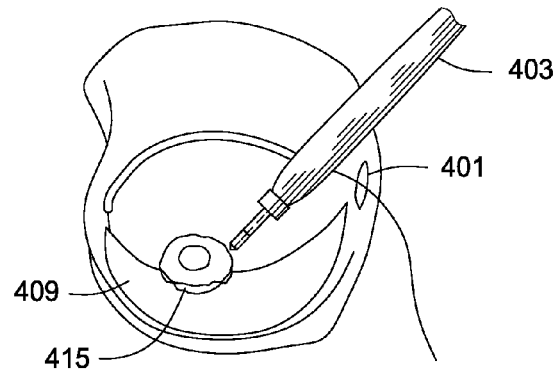
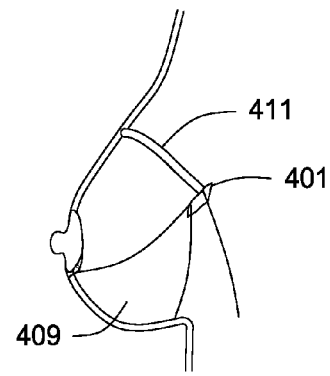
FIG. 4A    FIG. 4B
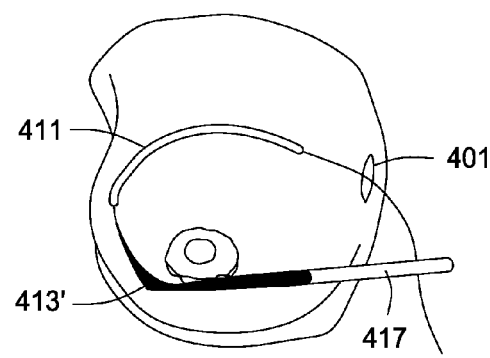
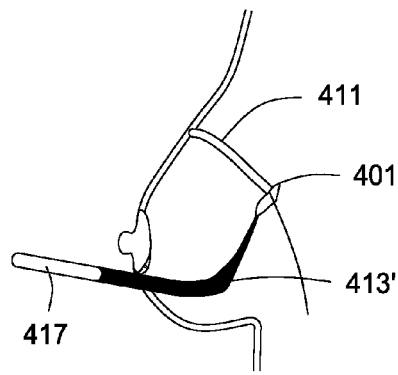
FIG. 4C    FIG. 4D
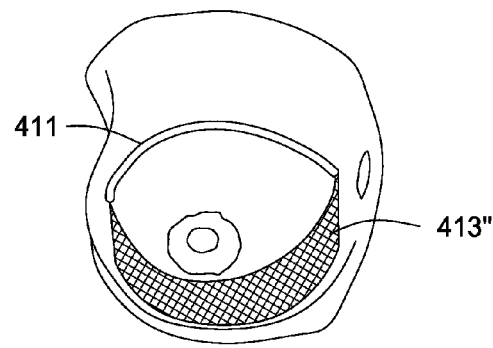
FIG. 4E

SYSTEMS AND METHODS FOR MASTOPEXY

RELATED APPLICATIONS

The present application is a continuation of U.S. Ser. No. 14/249,155, filed Apr. 9, 2014, which is a continuation of U.S. Ser. No. 13/413,770, filed on Mar. 7, 2012, now U.S. Pat. No. 8,858,629, and claims priority to U.S. Ser. No. 61/451,103, filed Mar. 9, 2011, and U.S. Ser. No. 61/604,242, filed Feb. 28, 2012, all of which are incorporated herein by reference.

FIELD OF APPLICATION

This application relates generally to systems and methods for mastopexy and breast lift.

BACKGROUND

Breast ptosis involves an inferior displacement or sagging of breast parenchyma accompanied by an inferior displacement of the nipple-areolar complex (NAC) with respect to the inframammary fold (IMF). Breast ptosis may be found in patients with normal breast size, with relatively small breast size (hypoplasia) or with enlarged breast size (hypertrophy). The combination of ptosis and hypoplasia may be found in the post-partum breast, as the relative breast enlargement of pregnancy and lactation recedes, leaving behind a stretched skin envelope that contains the involuted parenchyma. Hypertrophic breasts typically include some component of breast ptosis in addition to enlarged size.

Breast ptosis is categoried according to the position of the NAC relative to the IMF and relative to the lower pole of breast tissue. Grade 1 ptosis is considered mild, with the nipple just below the IMF but still above the lower pole. Grade 2 ptosis is considered moderate, with the nipple further below the IMF, but with some lower pole tissue below the nipple. Grade 3, severe ptosis, has the nipple well below the IMF, and no lower pole tissue below the nipple. Pseudoptosis, observed with postpartum breast atrophy, includes inferior pole ptosis, with the nipple positioned at or above the IMF.

Mastopexy is a surgical procedure performed to correct breast ptosis. Its goals are to restore the normal contour of the breast mound and to reposition the NAC. To achieve this goal, the excess breast skin is removed or tightened, the parenchymal volume is augmented or reduced as needed, and the NAC is repositioned. The choice of technique is based on the desired final breast size and the degree of ptosis. For minimal ptosis and breast hypoplasia, breast augmentation is sometimes employed in lieu of mastopexy even though it involves the use of a silicone implant. Breast augmentation involves the placement of a breast implant underneath the breast parenchyma, usually through an inframammary fold incision. The implant pushes the parenchyma up and out for a less ptotic and larger appearance. The projection is much more pronounced when the implants are placed in the subglandular position compared to the submuscular position.

When more ptosis correction is required, the traditional mastopexy employs NAC repositioning and/or skin resection. A variety of skin incisions may be used, each leaving its own characteristic scar pattern after healing. Skin incisions include the wise or anchor pattern, the circumareolar incision, and the periareolar incision.

Because it is a voluntary, cosmetic procedure, avoiding or minimizing skin incisions adds to the challenge of mastopexy surgery. Mastopexy surgery has traditionally been accompanied by considerable scarring. The extensive scars of the Wise pattern mastopexy, for example, may be necessary if major repositioning and resection is performed, but they represent a significant drawback to the procedure. Though endoscopic techniques have been devised for mastopexy procedures, open surgery is required in many cases to move the nipple, remove excess tissue, or recontour the breast mound. Even if the "anchor" scars of the Wise pattern can be avoided, other open mastopexy techniques still create visible scars on the breast.

The crescent, or periareolar incision may provide for the least noticeable scars; however, serious areola stretching or tissue necrosis is a not infrequent problem as all of the newly lifted parenchymal weight is supported by suture around the areola.

With traditional mastopexy procedures, the tightened skin envelope provides the main support for the lifted breast. Breast implants can be used to fill out the breast contour superiorly, this procedure is termed the augmentation-mastopexy. The augmentation-mastopexy procedure has higher risk of morbidity and twice the number of scars.

Breast flap repositioning can also be used to fill out the superior contour of the breast; however, this type of breast mound repositioning is a significantly more invasive and complex procedure that involves transposing lower pole tissue bulk and moving it superiorly and securing it to a deeper and higher tissue plane.

Irrespective of the type of mastopexy procedure performed, it is standard procedure that the tightened skin remains the primary support used to keep the breast mound elevated. As the lower pole skin stretches over time as it did in the first instance, ptosis can recur or pseudoptosis ("bottoming out") can take place. Placement of a breast implant leads to additional weight upon the skin of the lower pole, possibly leading to more rapid skin expansion and recurrent ptosis.

For retaining an upright configuration to the lifted breast and avoiding the post-operative sequelae of recurrent ptosis or pseudoptosis, or "bottoming out", certain authors have advocated the use of permanent prosthetics such as polypropylene mesh or silicone sheeting to reinforce the lower pole (see, for example, the Orbix breast lifting kit manufactured by Orbix Medical, Tel Aviv, Israel) or wrap the entire parenchyma (see, for example, the Breform™ device, manufactured by Aspide Medical, St. Etienne, France). Concerns about leaving foreign bodies permanently in the breast have limited the widespread adoption of these techniques somewhat. A permanent foreign body, according to the literature, is prone to infection and can facilitate a chronic inflammatory reaction. Furthermore, chronic foreign body reactions are often linked to hardening of the tissue and capsular contracture in the same manner as that associated with breast implants. Moreover, a permanent foreign body can interfere with breast cancer surveillance and can distort tissue planes if an oncological procedure is required.

Various permanent sheets such as polypropylene or polyester meshes have been wrapped around the parenchyma (see, for example, the Breform™ device, manufactured by Aspide Medical, St. Etienne, France), but lack an anchoring element that removes load from the skin of the lower pole, thus subjecting the wrapped breast not only to the potential chronic inflammatory response but also to the same ptotic forces as before surgery. Permanent silicone sheets have also been used to cradle the lower pole, which is then suspended from screws in the ribcage, placing all of the load force on one or two fixation points high above the nipple. Additionally, various minimally invasive mastopexy procedures are described in U.S. Pat. No. 7,670,372 to Orbix and Patent Publication No. 2008/0027273 to Gutterman.

More recently, allograft or xenograft products have been proposed as suitable to provide extra support for breast tissue or breast implants during post-mastectomy reconstruction. For example, acellular cadaveric dermal matrix or crosslinked bovine or ovine dermal matrix or collagen have been proposed. Acellular cadaveric dermal matrix has been used extensively in procedures to extend the skin flap or reposition the breast during reconstruction procedures. Depending upon the degree of processing involved in the formation of these constructs, they gradually degrade and sometimes resorb, and there is anecdotal evidence that they are replaced with tissue. If degradation occurs too quickly, though, these tissue matrices are not replaced by scar tissue and the patient can suffer recurrent ptosis and "bottoming out." And if they do not resorb or resorb quite slowly, there is evidence in the literature that they cause increased seroma formation and infection compared to natural tissue flaps. As with the synthetic mesh, these devices require full open procedures and do not alleviate scarring.

A further challenge for mastopexy surgeons is the evolving aesthetic of the upper pole. While traditional mastopexy techniques focused on elevation of the ptotic NAC and lower pole, there is contemporary demand for a fuller look to the upper pole as well. Upper pole fullness, commonly seen following breast augmentation surgery with silicone and shaped implants, has become the paradigm to which some women aspire when thinking about breast surgery. This aesthetic can motivate a mastopexy patient to seek a fuller upper pole in conjunction with a lifted lower pole, a tightened inferior skin envelope and a repositioned NAC.

There remains a need in the art, therefore, for systems and methods of mastopexy that provide the creation or restoration of an uplifted breast shape in a more durable way, as well as preventing post-operative pseudoptosis or recurrent ptosis without compromising the safety or aesthetic quality of the surgical outcome. Desirably, this solution would avoid the potential complications that can accompany the standard mastopexy procedure, permanent mesh placement and/or breast implants while providing long-lasting support for the reshaped breast. For example, it would be desirable to deploy soft-tissue promoting resorbable scaffolds and supports or a long-lasting resorbable matrix that is elastic enough to permit a natural dynamic appearance to the breast via smaller incisions such that, once placed, they offer a good balance between scarring, tissue ingrowth and ultimate resorption. There is a further need in the art for mastopexy techniques that can provide a fuller contour for the upper pole, to satisfy patient aesthetic demands. And, as previously mentioned, avoiding or minimizing scars remains a desirable goal.

SUMMARY OF THE INVENTION

Disclosed herein, in embodiments, are mastopexy systems, comprising an insertion device, a suspension strut, and a lower pole support, wherein the insertion device inserts the suspension strut into a breast, wherein the suspension strut provides superior pole projection and further provides attachments for the lower pole support, and wherein the lower pole support provides uplift for the lower pole of the breast.

In embodiments, a method for preventing ptosis recurrence is disclosed. The method comprises removing some of the parenchymal load from the skin envelope. In embodiments, the suspension strut comprises a biodegradable material. In embodiments, the lower pole support comprises a biodegradable material. In embodiments, the lower pole support comprises a mesh material. In embodiments, the lower pole support is a unitary conformable mesh or sheet. Also disclosed herein are kits comprising the aforesaid mastopexy system.

Further disclosed herein, in embodiments, are methods for elevating a lower pole of a female breast, comprising providing an insertion device, a suspension strut, and a lower pole support, inserting the insertion device into the breast to define a channel in a superior pole of the female breast, delivering the suspension strut into the channel, thereby applying a force to the superior pole to produce superior pole projection, positioning the lower pole support beneath at least a portion of the lower pole, and attaching the lower pole support to the suspension strut with sufficient tension to elevate the lower pole.

Further disclosed herein, in embodiments, are methods for creating a subcutaneous space between the skin and the parenchyma around the lower pole of the breast; inserting a support in the lower pole of the breast; and elevating the lower pole of the breast using the support and by attaching straps of the support to an upper pole suspension strut and/or affixation points in soft or hard tissue.

Further disclosed herein, in embodiments, are mastopexy implants comprising a central body region and a plurality of straps extending therefrom. The implant can be inserted into a subcutaneous pocket in an inferior portion of the breast and secured at multiple points in the soft and hard supportive tissue surrounding the parenchyma.

In embodiments, a mastopexy implant comprises a unitary flexible bioabsorbable mesh. The mesh includes a substantially 2D configuration in the shape of a central region and a plurality of discrete straps or extension members extending therefrom, and the mesh further has a second 3D dimensional configuration when deployed so as to secure the breast. When deployed the central region at least partially covers a lower pole of the breast and at least two of the extension members extend superiorly around and away from the NAC. Additionally, at least two extension members extend inferiorly towards the IMF. The implant lifts the lower pole of breast when affixed to the supportive tissue.

In embodiments, a mastopexy implant comprises sheet or mesh having a plurality of regions or sections. A first or upper region is disposed above a second or lower region. The region is sized to substantially span a portion of the lower pole of the breast and to not cover the NAC. The upper region comprises a plurality of upper attachment end portions for attaching to supportive tissue of the patient in the vicinity of a superior side of the breast. The lower region comprises a plurality of lower attachment end portions for attaching to supportive tissue in the vicinity of the IMF so as to secure the breast in the second position when attached to the supportive tissue. The upper region may have a wide variety of shapes including an elliptical, football, or other type of shape. The lower region may comprise a similar or different shape, and a similar or different size than the upper region.

Further disclosed herein, in embodiments, is a method and tools for elevating the lower pole of the breast comprising the steps of creating at least one incision preferably in the lateral, medial, inframammary and/or periareolar areas of the breast; creating a subcutaneous pocket with a dissection or subscision tool; inserting and deploying the lower pole support from the insertion device such that straps of the lower pole support are placed over the breast parenchyma, unfurled, and anchored in multiple places to elevate the lower pole of the breast and remove load from the skin envelope to prevent recurrent ptosis.

Further disclosed herein, in embodiments, is a mastopexy system comprising an insertion tool containing a preloaded lower pole support with multiple straps.

Further disclosed herein, in embodiments, is a mastopexy system comprising a lower pole support with multiple straps wrapped around an insertion tool

BRIEF DESCRIPTION OF THE FIGURES

FIGS. 2A-D illustrate schematically the passage of an embodiment of an insertion device.

FIGS. 4A-E illustrate schematically the positioning of an embodiment of a lower pole support.

DETAILED DESCRIPTION

Figure 1A:
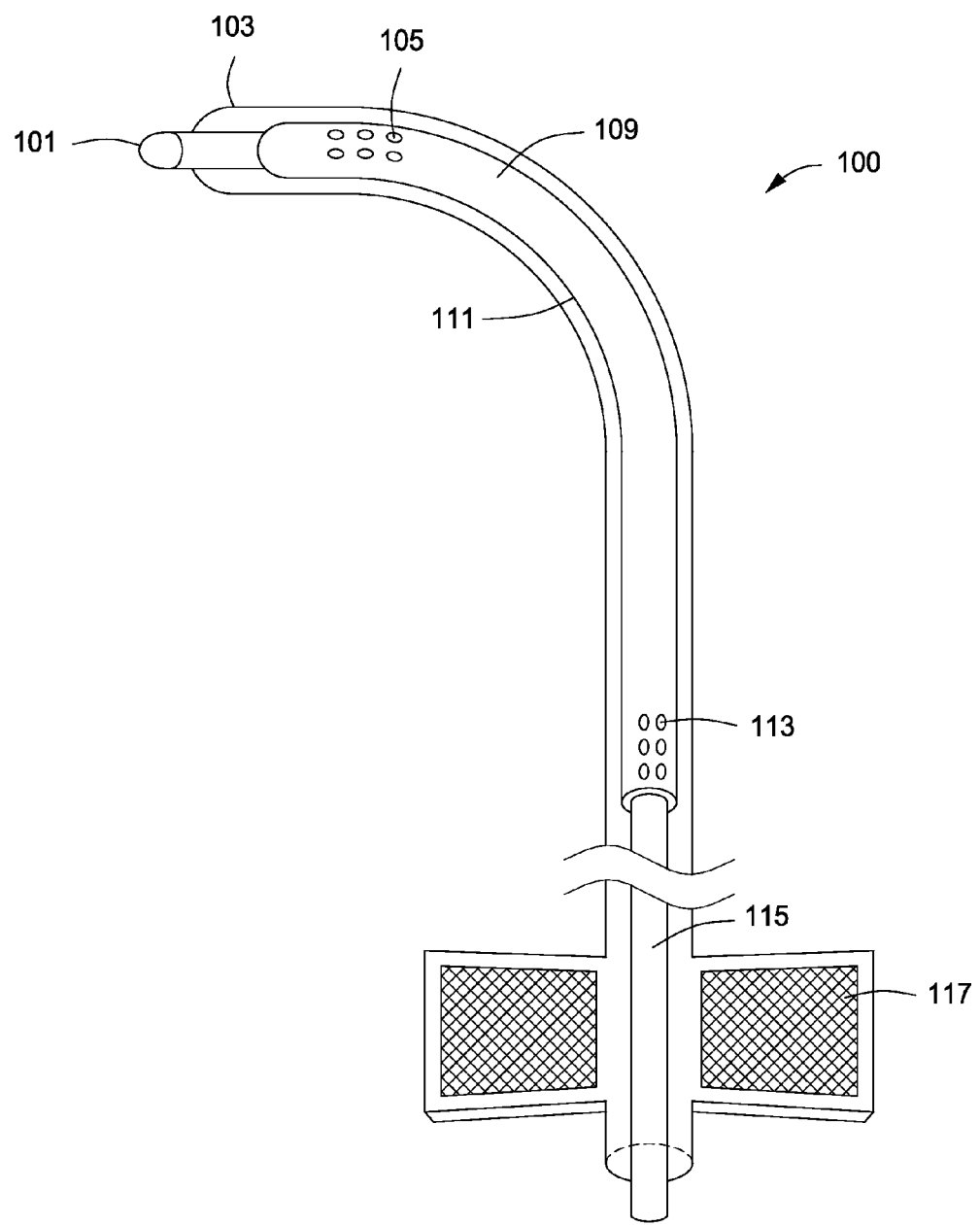
FIG. 1A shows an embodiment of an insertion device.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Disclosed herein are products, systems and methods for performing mastopexy surgery of a female breast. As used herein, the term "mastopexy" refers to a procedure that modifies and/or repositions a portion of the female breast, often for the purposes of maximizing the aesthetics of the breast, which repositioning may include a superior repositioning of a lower portion of the breast and/or a superior repositioning of a nipple-areolar complex (NAC). Optionally, the mastopexy can include configuring the breast in an aesthetically desirable manner, for example by enhancing projection of the superior pole of the breast or the subareolar central mound of the breast. Advantageously, the systems and methods disclosed herein use minimally invasive technologies in order to accomplish a mastopexy with reduced scarring as compared to traditional, open surgical procedures.

Mastopexy System

A system for performing a mastopexy in accordance with the present disclosure can comprise an insertion device, and a lower pole support. In another embodiment, a system comprises an insertion device, a suspension strut, and a lower pole support. In another embodiment, the suspension strut and the insertion device are one and the same. A method for performing a mastopexy in accordance with the present disclosure can include the steps of creating a channel for placement of the suspension strut by manipulating the suspension strut through tissue, positioning the suspension strut with the insertion device if two separate entities, and attaching the lower pole support to the suspension strut under sufficient tension to support the lower pole of the breast and project the upper pole of the breast. In embodiments, the systems disclosed herein can be prepared as kits, with the individual components arranged for ready access by a surgeon. Kits can be prepared with disposable components or reusable components, and the access tube can be preloaded with certain components. Kits can be prepared for sterilization, or they can be pre-sterilized.

As shown in FIG. 1a, an insertion device 100 comprises, in embodiments, an access tube 103 having an inner passageway through which can be passed other components. For example, a dissector 115 can be passed through the access tube that will permit the surgeon to dissect a space beneath the skin or within the breast tissue for the subsequent passage of the suspension strut as described below. In embodiments, the dissector 115 can be configured for blunt dissection. In other embodiments, the dissector 115 can comprise an electrocautery mechanism or other mechanism for hemostasis. In other embodiments, the dissector 115 can comprise a liposuction component to be used itself for dissection or as an adjunct to other dissection mechanisms. The dissector 115 can comprise a specialized tip 101 to facilitate dissection, and the tip 101 can comprise electrocautery or other hemostatic devices. In embodiments the dissector 115 can be a rigid device, pre-formed in a preselected shape. In other embodiments, the dissector 115 can be flexible or formable, so that it can be configured by the surgeon into a desirable shape.

The dissector 115 can cooperate with a suspension strut 111 to be inserted over or alongside the dissector 115 once the dissection has been accomplished. The positioning of the suspension strut 111 over the dissector can be accomplished by a combination of advancing the suspension strut 111 forward (using, for example, a pusher or plunger (not shown)) and/or retracting the access tube 103 and the dissector 115.

In an embodiment, the suspension strut 111 is positioned within the access tube 103, over the dissector 115, during the entire process of dissection, to be positioned using the insertion device 100 once the dissection is completed. In another embodiment, the dissector 115 within the access tube 103 is used to create the submammary or inframammary pocket, following which the dissector 115 is withdrawn and the suspension strut 111 is positioned. In other embodiments, the suspension strut 111 can be passed over the dissector 115 after withdrawal of the access tube 103, with the dissector 115 acting as a guidewire for suspension strut 111 positioning.

While the insertion process has been described using non-visualized dissection, the insertion device 100 can also, optionally, include visualization technologies, for example endoscopic visualization or a lighted tip whose position can be followed while the insertion device 100 is used.

In certain embodiments, the insertion device 100 is advanced through a single incision (positioned medially or laterally, or otherwise at the surgeon's discretion), with the suspension strut 111 being left behind after an appropriate pocket is dissected. In other embodiments, the insertion device 100 may be inserted through one incision for pocket dissection using blunt or electrocautery dissection, where a sharpened tip 101 is then used to punch through from inside the breast to the outside to create a second stab wound on the opposite side of the breast. For example, if a medial access incision had been used, a lateral or axillary stab wound could be created, or vice versa. This technique would permit the creation of a second access site for further manipulation of the suspension strut 111 or for its affixation to the chest wall or breast tissue or other bony or soft tissue, or for its attachment to the lower pole support as described below.

If two incisions are used (i.e., a proximal incision and a distal stab wound, as described above), a retrograde grasper (not shown) can be passed through the second incision to grasp the suspension strut 111 or to grasp a suture or pullwire 109 attached thereto to pull the suspension strut 111 into position within the dissected pocket.

In certain embodiments, a suture or pullwire 109 attached to the suspension strut 111 can be used to affix the suspension strut 111, with the suture or pullwire 109 being used to attach the distal end of the suspension strut 111 to surrounding tissues or to an affixation anchor (not shown) that has been previously positioned in the tissues. In other embodiments, the suture or pullwire 109 can be used to attach the distal end of the suspension strut 111 to the lower pole support mechanism that is positioned as described below.

Figure 1B:
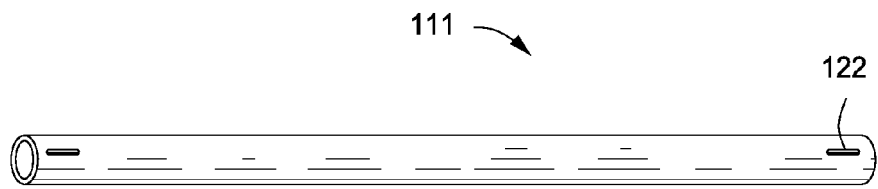
FIGS. 1B-1D illustrate various suspension struts.
Figure 1C:
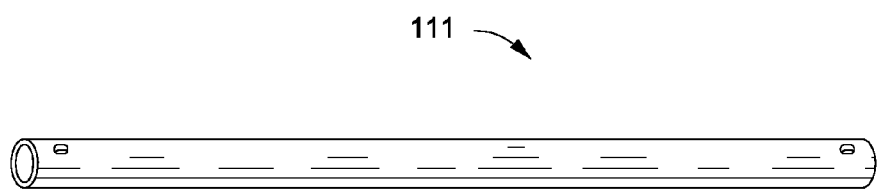
Figure 1D:
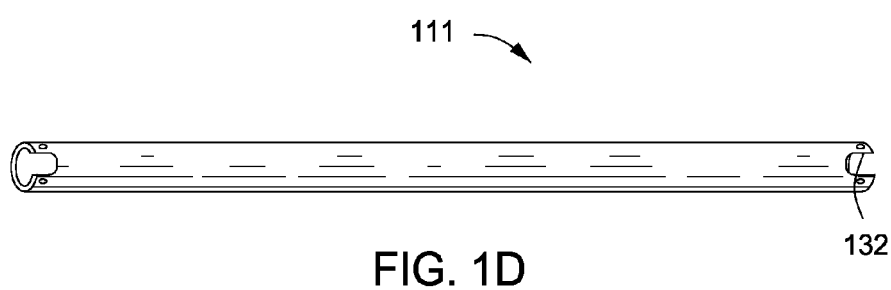

Also for affixation, a distal affixation mounting 105 and a proximal affixation mounting 113 can be provided. As depicted in FIG. 1a, the affixation mountings 105 and 113 can be configured as holes or other apertures through which sutures, staples, or other anchoring mechanisms can be placed, to allow attachment of the suspension strut 111 to soft tissues, hard tissues, affixation anchors (not shown), and/or the lower pole support mechanism, for example using sutures that are inserted by the surgeon intraoperatively. Non-limiting examples of suspension devices are shown in FIGS. 1B-1D. FIG. 1B shows a strut 111 including a slot or slit 122 for affixation. The slit may receive a suture, tongue, tab, or another feature for interlocking with an anchor or the lower pole support. FIG. 1D shows a strut 111 comprising a recess or groove 132 for accepting an anchor, mount, or tab device for affixation. A wide variety of structures may be incorporated for holding, affixing, and connecting to support tissue, anchors, and the lower pole devices.

In other embodiments, the affixation mountings 105 and 113 can be configured as snaps, clasps, anchors, fasteners, tacks, or the like, to allow direct or indirect attachment to soft tissues, hard tissues, tissue-mounted affixation anchors, and/or the lower pole support mechanism. In an embodiment, for example, one or both of the affixation mountings 105 and 113 can be configured as an arrow-tip or flange that can snap-fit into a mating anchor on the lower pole support mechanism. A variety of affixation mountings for attachment to tissues or to other components of the mastopexy system are within the scope of the present disclosure and can be envisioned by practitioners of ordinary skill in the art.

As shown in FIG. 1a, the insertion device 100 can be provided with a handle 117 that is graspable by a surgeon during the insertion process. A handle 117 can be any structure incorporated into or attached onto the proximal end of the insertion device 100 providing the surgeon with a firm surface for gripping and manipulating the insertion device 100. While the handle 117 illustrated in FIG. 1a is shaped as two wings perpendicular to the shaft of the access tube 103, a handle 117 can be shaped as a unilateral structure (e.g., a pistol grip), or as any other structure that permits secure grasp and manipulation. For example, a handle can comprise a series of projections and indentations that provide the surgeon's hand with purchase on the proximal end of the insertion device 100. A variety of handles 117 for the insertion device 100 are within the scope of the present disclosure and can be envisioned by practitioners of ordinary skill in the art.

As shown in FIGS. 2a-d, an insertion device 205 can be inserted into the breast 200 to position the suspension strut 311 as shown in FIGS. 3 a-c. With reference to FIG. 2a, a female breast 200 is depicted having an access incision 201 made through the skin in the parasternal region. In other embodiments, the access incision 201 can be placed in the lateral aspect of the breast 203, in the periareolar skin 207 as shown in FIG. 2a, in the axilla (not shown) or in the inframammary fold beneath the breast (not shown). The curvature of the insertion device 205 is suitable for use through access incisions in the superolateral or superomedial skin of the breast, although in other embodiments an insertion device 205 can be configured for use through an incision in other areas of the breast skin. For exemplary purposes, the mastopexy system and method will be described and illustrated using the parasternal access incision 201, although it is understood that other access incisions could be used as well.

As shown in FIG. 2b, the insertion device 205 enters the access incision 201, directed laterally. FIG. 2c and FIG. 2d show the trajectory of the insertion device 205 as it tunnels a path below the breast tissue, just superior to the pectoralis fascia, or within the breast tissue. The trajectory 209 of the path and its inframammary or subglandular positioning is determined by the surgeon based on pre- and intra-operative assessment of the patient. As shown in these Figures, the insertion device 205 follows the trajectory 209 determined by the surgeon, using blunt dissection, electrocautery, sharp dissection, balloon dissection, or some combination of these or other tissue-displacing techniques (guided, e.g., by palpation, indirect visualization or direct visualization) to create a pocket along the trajectory 209 that will house the suspension strut, as shown below in more detail. In the depicted embodiment of FIG. 2b, the insertion device 205 can act as a guide for the insertion of the suspension strut, as described below.

It is understood that the insertion device 205 can include other features, for example, a visualization device (not shown) for providing a direct image of the procedures taking place. In embodiments, the insertion device 205 can include other trackers, such as a light visible externally, or an electromagnetic tag, or the like, that allows determination of the position of the tip of the insertion device 205 using visualization or using positioning identification technologies. In embodiments, the insertion device 205 can include a balloon or other dissecting mechanism to permit the dissection of the pocket or tissue path for the suspension strut.

In embodiments, the percutaneous access incision 201 can be created as a stab wound by a needle, followed by a guidewire that allows placement of the insertion device 205. In an exemplary embodiment, the insertion device 205 can be directed along a predetermined trajectory 209 with the assistance of balloon dissection or hydrodissection. In an exemplary embodiment, the dissection process can be directly observed, for example by a fiberoptic visualizing scope.

In embodiments, a suspension strut 311 can be fabricated from a number of biodegradable materials. Optionally, the suspension strut 311 can include one or more pharmacologically active agents capable of imparting local or systemic effects. As used herein, the term "biodegradable" refers to a material that, when placed in a human or animal body, is hydrolytically labile, oxidatively labile, susceptible to enymatic activity, or the like (collectively, "biodegrading actions"), where such a biodegrading action leads to the partial or complete breakdown of the material within the human body. Materials, e.g., polymers, that are biodegradable have variable resorption times following their breakdown, depending on local and systemic factors within the body and depending on characteristics of the breakdown product like their size and chemical composition.

Materials for use by these systems and methods are, desirably, biocompatible. As used herein, the term "biocompatible" refers to a material that is compatible with living tissue or a living system so that it is acceptable for use in a human or animal body. A biocompatible material, for example a biocompatible polymer, does not cause physiological harm to the body to a significant or unacceptable extent. For example, a biocompatible material may be non-toxic, or otherwise not injurious to the living tissue or system, or it may not cause significant immunological or inflammatory response by the host.

A number of biodegradable materials can be useful, either as single agents or in combinations, for fabricating the suspension strut 211. In selecting polymeric materials for the suspension strut 211, the glass transition temperature (Tg) may be considered, as well as the compatibility of the material with pharmacological agents that may be optionally added to it. In embodiments, a polymer will be selected for the suspension strut 211 that is readily fabricated into the desired shape. For example, polymers with a sufficient difference between their melting temperature and decomposition temperature can be molded or extruded into tubular or cylindrical shapes.

A number of biodegradable polymers suitable for use in accordance with these systems and methods will be familiar to those of ordinary skill in the art. Processing methods and coating methods for those polymers are, similarly, familiar. As examples, polymers such as the following can be used: polylactic acid, polyglycolic acid and copolymers and mixtures thereof such as poly(L-lactide) (PLLA), poly(D,L-lactide) (PLA), polyglycolic acid or polyglycolide (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), poly(D,L-lactide-co-caprolactone) (PLA/PCL) and poly(glycolide-co-caprolactone) (PGA/PCL); polyhydroxyalkanoates, poly(oxa)esters, polyethylene oxide (PEO), polydioxanone (PDS), polypropylene fumarate, poly(ethyl glutamate-co-glutamic acid), poly(tert-butyloxy-carbonylmethyl glutamate), polycaprolactone (PCL), polycaprolactone co-butylacrylate, polyhydroxybutyrate (PH BT) and copolymers of polyhydroxybutyrate, poly(phosphazene), poly(phosphate ester), poly(amino acid), polydepsipeptides, maleic anhydride copolymers, polyiminocarbonates, poly[(97.5% dimethyl-trimethylene carbonate)-co-(2.5% trimethylene carbonate)], poly(orthoesters), tyrosine-derived polyarylates, tyrosine-derived polycarbonates, tyrosine-derived polyiminocarbonates, tyrosine-derived polyphosphonates, polyethylene oxide, polyethylene glycol (PEG), polyalkylene oxides (PAO), hydroxypropylmethylcellulose, polysaccharides such as hyaluronic acid, chitosan and regenerate cellulose, and proteins such as gelatin and collagen, and mixtures and copolymers thereof, among others as well as PEG derivatives or blends of any of the foregoing. Desirably, polymeric materials can be selected for these systems and methods that have good strength retention, such as polydioxanone, silk-based polymers and copolymers, poly4-hydroxybutyrates, and the like. Suitable biocompatible polymers can be used alone or in blends with other biocompatible materials.

Desirably, the material selected for the suspension strut will be conformable (either before or after insertion into the body) into a shape permitting superior pole projection. Moreover, the material selected for the suspension strut will desirably have sufficient strength and durability to sustain the projection of the superior pole. Without being bound by theory it is anticipated, in embodiments, that the presence of a short-term inflammatory response and collagen deposition, all attributable to a stimulatory effect accompanying the biodegradability process for the suspension strut can provide additional fullness and long-term support.

The suspension strut 311 can be shaped as a cylindrical structure, as a ribbon, or as any other shape that will flex in response to the weight provided by the lower pole support, as described below, while imparting the desired shape to the upper pole of the breast. In embodiments, the suspension strut 311 comprises more than one shape, for example a central flat portion and cylindrical or tapered side portions, and the suspension strut 311 may comprise more than one material having specific properties.

Figure 3A:
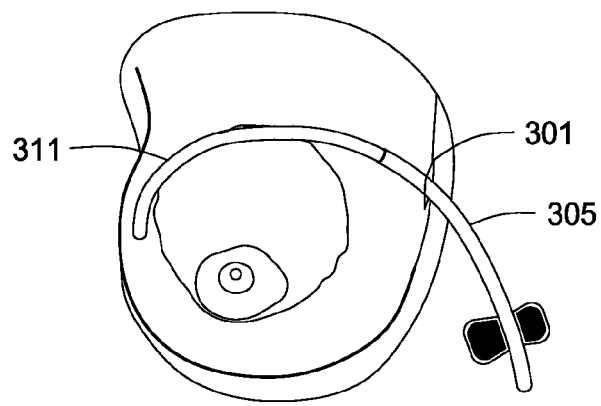
FIGS. 3A-C illustrate schematically the placement of an embodiment of a suspension strut.
Figure 3B:
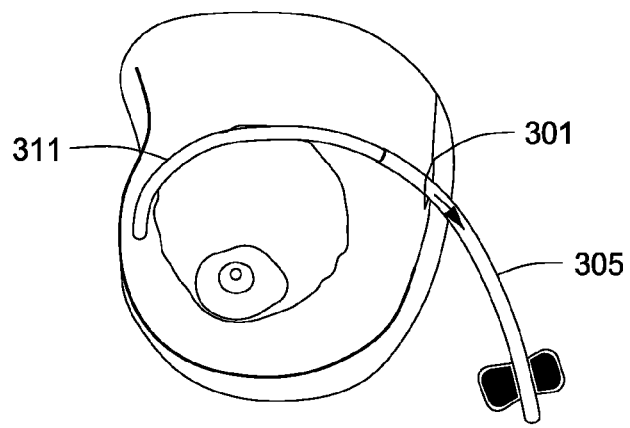
Figure 3C:
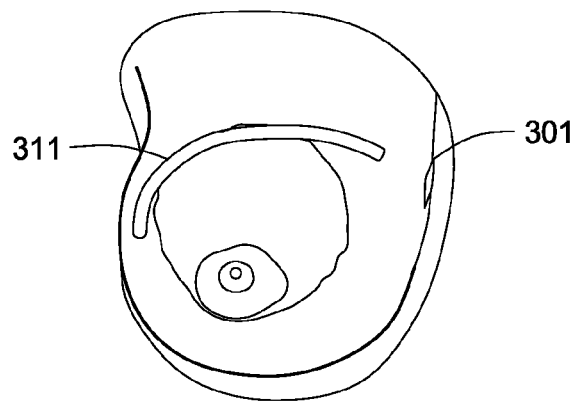

As shown in FIG. 3a, the suspension strut 311 can be passed through a hollow passageway within the insertion device 305 as depicted. Alternatively, the insertion device 305 can be used like a guidewire, with the suspension strut 311 passed over it (not shown). As shown in FIGS. 3a-3c, a single access incision 301 can be used for the entry of the insertion device. In these Figures, the access incision 301 is shown on the medial or parasternal aspect of the breast. It is understood that the access incision 301 can be positioned on the lateral aspect of the breast, on the chest wall, in the axilla, or in other regions (inframammary fold, periareolar, etc.) familiar to those of ordinary skill in the art. An additional access incision (not shown) can be used in any of these locations to assist in placement or positioning of the suspension strut 311.

When the suspension strut 311 has been appropriately positioned, as shown in FIG. 3*b*, the insertion device 305 can be removed along its path of entry. FIG. 3*c* shows the suspension strut 311 in position within the breast. In patients where increased upper pole fullness is desired, the suspension strut 311 can be positioned so that it projects anteriorly rather than lying beneath the breast tissue on the pectoral fascia. The positioning of the suspension strut 311 is typically determined by the surgeon planning and executing the procedure. Achieving anterior projection for the suspension strut 311 may require dissection through the breast tissue when the suspension strut is initially placed.

Lower Pole Support

FIGS. 4 *a-e* show, schematically, certain steps of a procedure for positioning a lower pole support 413 in combination with other steps of the mastopexy. As shown in FIG. 4*a*, in embodiments, a perioareolar incision 415 can be made, permitting access to the lower pole of the breast. Through this incision, dissection can be carried out, for example with an electrocautery device 403 to produce an area of subcutaneous dissection 409. FIG. 4*a* shows, in an embodiment, the extent of subcutaneous dissection 409 in an anterior view, and FIG. 4*b* shows, in an embodiment, the extent of the subcutaneous dissection 409 in a lateral view. However, as will be discussed in more detail herein, additional dissection can be carried out to create different shapes of pockets including deep pockets and channels for accommodating elongate extension members, bands, ribbons, and straps of the lower pole support. In embodiments, dissecting may be carried out to extend the pocket or channel to the chest wall (i.e., proximal of, or posterior to, the breast parenchyma). In embodiments, dissection may be carried out to extend channels upward in a radial manner toward the chest wall medial and lateral to the breast.

FIG. 4*b* also shows, schematically, the positioning of a suspension strut 411 to effect increased anterior projection, although other positions for the suspension strut 411 are also in accordance with this disclosure (i.e., a flatter position with less anterior projection). The amount of anterior projection for the suspension strut 411 can be determined at the time of surgery in accordance with the aesthetic desires of the patient, as discussed preoperatively. While the depicted embodiment shows the suspension strut 411 in a subcutaneous position, the suspension strut 411 can also be positioned within the breast parenchyma or below the breast parenchyma, as described previously.

As shown in FIGS. 4*c* and 4*d*, a lower pole support 413' can be positioned within the breast so that it occupies some or all of the subcutaneous dissection area shown in the preceding FIGS. 4*a* and 4*b*. Also as shown in FIGS. 4*c* and 4*d*, the lower pole support can be inserted or repositioned, or fixed through the periareolar, medial, or lateral incisions (e.g., 401, 415). In embodiments, a positioning tool 417 can insert the lower pole support 413' within the dissected area via the lateral or medial incisions and can further direct the lower pole support 413 into its deployed shape 413", as shown schematically in FIG. 4*e*. In an embodiment, the lower pole support 413 can be flexible and capable of being rolled cylindrically within a hollow positioning tool 417. In an embodiment, the lower pole support 413 can be rolled around the outside of a positioning tool.

Deployment of the lower pole support 413 takes place in part by withdrawing the positioning tool 417 and leaving the lower pole support 413 behind. In certain embodiments where a periareolar incision is used for the insertion of the positioning tool 417, only a part (e.g., a lateral part) of the lower pole support 413 may be positioned by using the tool, with a portion of the lower pole support 413 (e.g., the medial part) remaining outside the incision and requiring subsequent manual positioning.

In another practice, the incision used to position the suspension strut 411 can be used to position the lower pole support 413 after the subcutaneous dissection 409 has been accomplished in the lower pole. The positioning tool 417 can access the entire subcutaneous dissection 409 through the initial incision 401 and can deploy the lower pole support 413 from distal to proximal within the subcutaneous dissection space 409. This practice minimizes exposure of the lower pole support 413 to the skin itself, potentially reducing the possibility of contamination. In those practices where two incisions have been used for placement of the suspension strut 411, the two incisions can be used for more accurate positioning of the lower pole support 413.

In embodiments, it is understood that an access incision can be positioned on the lateral aspect of the breast, on the chest wall, in the axilla, or in other regions (inframammary fold, periareolar, etc.) familiar to those of ordinary skill in the art. An additional access incision (not shown) can be used in any of these locations to assist in placement or positioning of the lower pole support. In embodiments, the positioning tool can be inserted through the lateral incision 401 proceeding all the way across the lower pole and positioned by manual guidance using forceps or the like through a second medial incision (not shown) in the breast. In embodiments, the distal positioning of the lower pole support 413 may be accompanied by an affixation, either to the patient's hard or soft tissues or to the suspension strut 411, or both. In embodiments, the suspension strut 411 is formed with a proximal and/or distal affixation mounting that includes a region for attaching, affixing or seating the lower pole support 413. For example, various mounting structures are shown in the struts depicted in FIGS. 1A-1D, described above.

In embodiments, the suspension strut 411 is equipped with a suture, a clip, a fastener or other attachment mechanism at each of its ends to allow the affixation of the lower pole support thereto. In embodiments where two incisions have been used for the placement of the suspension strut 411, these incisions can be used to facilitate the attachment of the suspension strut 411 to the lower pole support 413, for example by allowing the tying of a suture to attach these two components to each other. Additionally, in embodiments, two or more portions of the lower pole support can be affixed to the soft or hard tissue via a clip, suture, or anchor through the two incisions medial and lateral.

In embodiments, the distal positioning of the lower pole support 413 is accompanied by an affixation, either to the patient's hard or soft tissues or to the suspension strut 411, or both. In embodiments, the suspension strut 411 is formed with a proximal and/or distal affixation mounting that includes a region for attaching, affixing or seating the lower pole support 413. In embodiments, the suspension strut 411 is equipped with a suture, a clip, a fastener or other attachment mechanism at each of its ends to allow the affixation of the lower pole support thereto. In embodiments where two incisions have been used for the placement of the suspension strut 411, these incisions can be used to facilitate the attachment of the suspension strut 411 to the lower pole support 413, for example by allowing the tying of a suture to attach these two components to each other.

Optionally, a light source may be inserted within the subcutaneous dissection 409 along with other appropriate optics to permit direct visualization of the attachment of suspension strut 411 to lower pole support 413.

In embodiments, the lower pole support can be self-deploying or self-configuring. For example the lower pole support may be comprised of shape-memory materials or from other plastic or metallic materials that maintain a predetermined shape upon the release of a constraining force. In embodiments, the lower pole support 413 can be inserted, positioned and deployed without a positioning tool 417, using standard surgical instruments. In embodiments, the lower pole support 413 is crescent-shaped. In other embodiments, the lower pole support 413 is rectangular or any other shape. The lower pole support 413 may be deployed only across the central region of the lower pole to provide support over a relatively small area within the breast, or it can occupy a wider area from the medial breast to the lateral breast. In an embodiment, the lower pole support 413 can act as an "internal brassiere," elevating and shaping the breast in an aesthetically desirable way.

Figure 4F:
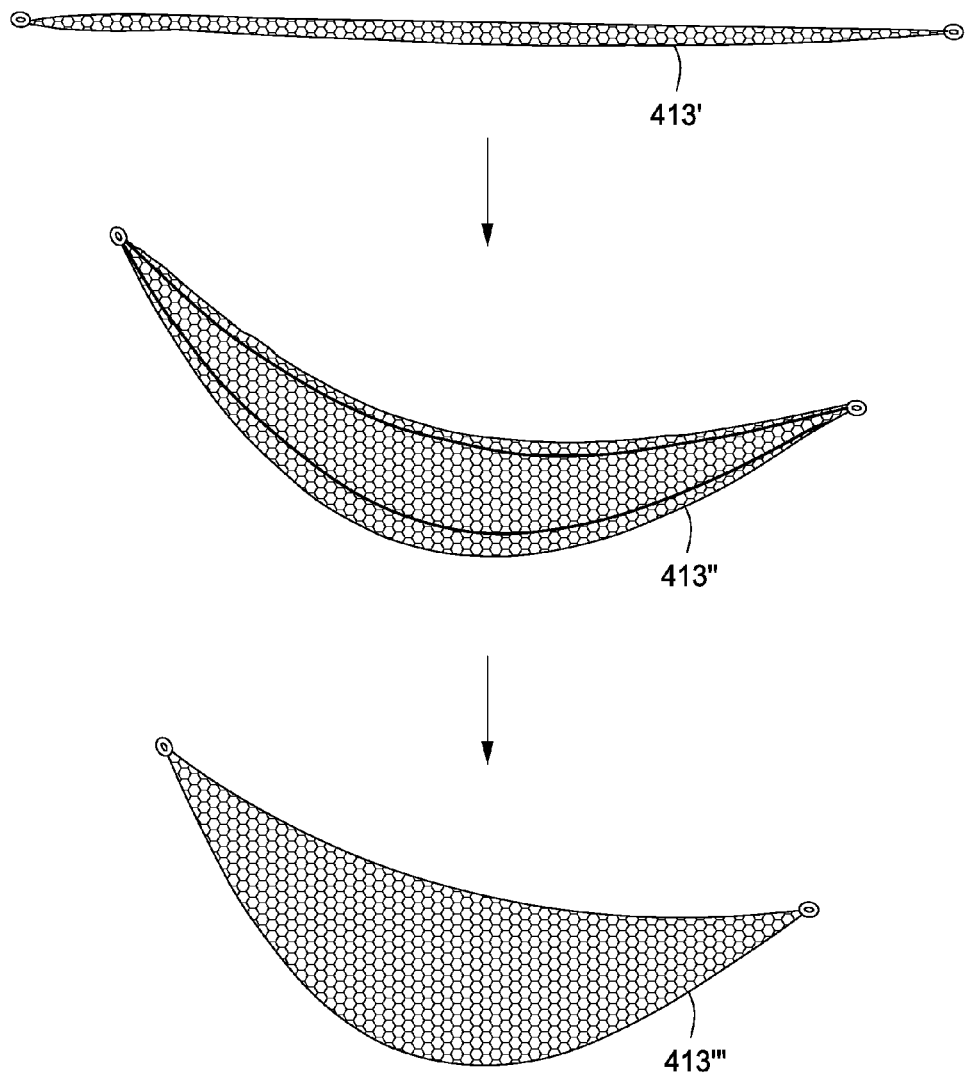
FIG. 4F illustrates a lower pole support transitioning from a collapsed configuration to a deployed shape.

FIG. 4f shows a crescent-shaped lower pole support transitioning from a first low profile or rolled configuration to a deployed shape. In particular, lower pole support 413' is shown in a rolled or collapsed configuration. Lower pole support 413" illustrates an intermediate configuration. Lower pole support 413'" illustrates a final deployed shape or configuration. The lower pole support 413 in FIG. 4f is shown with the environment removed for clarity. Additionally, it is to be understood that the shapes and configurations may differ than the embodiment shown in FIG. 4f. The shapes may vary widely and the invention is only to be limited to that recited in the appended claims.

Figure 5A:
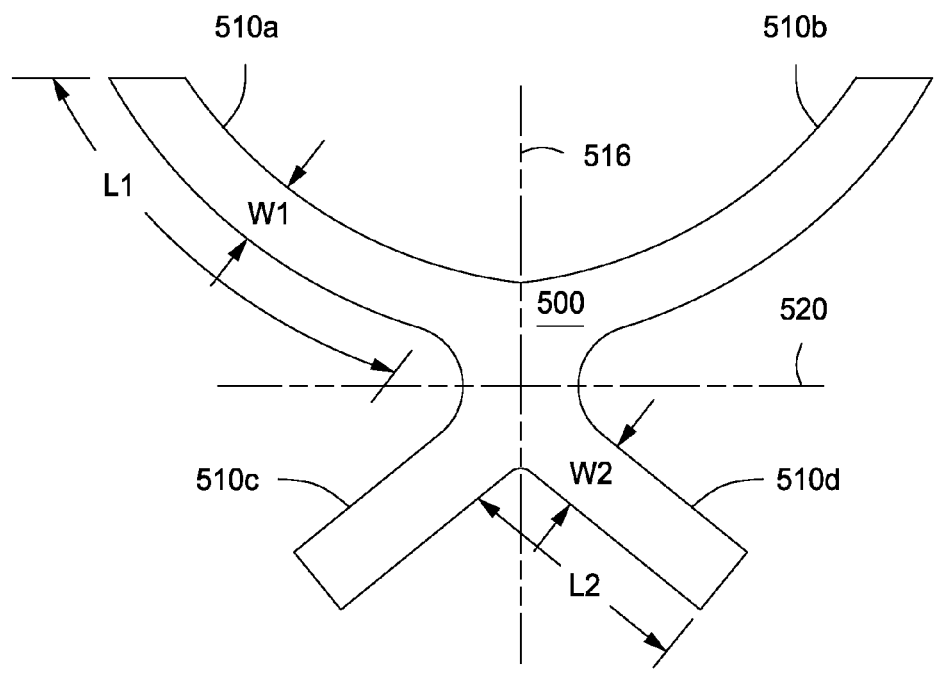
FIGS. 5A and 5B illustrate lower pole supports with multiple straps.

FIG. 5A illustrates another lower pole support 500 for lifting or securing breast tissue. The support 500 is shown in an unrolled state, e.g., in an intermediate state after manufacture yet prior to being loaded into the insertion device as described above.

The support 500 is shown having a roughly X-shape. Four straps or bands 510 *a,b,c,d* extend from a central body portion. Although four straps or bands 510 are shown in the support 500 of FIG. 5A, the number of straps may vary and in embodiments, the support may include 2, 3, 4, 5, or more straps and as many tissue affixation points. Support 500 is shown having a vertical axis of symmetry 516. Each side of the vertical axis of symmetry 516 consists of a diagonally downward slanted leg 510 *c,d* and a concave upward arm 510 *a,b* extending from a body. The body serves to support the lower pole when deployed and preferably has a size to uniformly and aesthetically shape the breast. The area of the central body region may vary and range from, for example, 1 to 15 sq. cm.

The halves separated by the horizontal axis 520, however, differ. The larger superior half has longer straps 510*a*, 510*b* than lower straps 510*c*, 510*d*. As will be described in more detail below, the longer straps serve to cover more breast volume above than below. The legs 510*c,d* are shorter than the arms.

Exemplary lengths of the legs range from about 1 to 15 cm and preferably are about 10 cm. Exemplary lengths of the arms may vary and range from about 3 to 30 cm and preferably are about 16 cm.

In some embodiments, the ratio of leg to arm length is 2:1.

The width of the legs range from about 0.25 to 5 cm and preferably are about 0.5 cm. The width of the arms may also vary and range from about 0.25 to 5 cm and preferably are about 0.5 cm. In some embodiments, the bands have a constant width. In other embodiments, the bands have a width that varies. The bands may comprise end portions that are straight, taper, or that terminate at a point.

It is to be understood that although the band and strap shape may vary widely, by "band" or "strap" it is meant to exclude the shape of a suture. The band and straps of the lower pole support have a different aspect ratio than that of a suture. For example, an exemplary aspect ratio (width/thickness) ranges from 5/1 to 500/1. Additionally, in embodiments, the band and straps may be integral with the body of the support. The support may consist of one unitary structure.

In embodiments, the support 500 and straps 510 are flexible, conformable, and thin. The support 500 may be made from various materials and may comprise materials as described herein in connection with other embodiments of the invention. In one embodiment, the support 500 comprises a 2-dimensional poly-4-hydroybutyrate (P4HB) polymer mesh construct. An example of a suitable mesh is the TephaFlex™ manufactured by Tepha Inc., Lexington, Mass. However, the invention is not so limited. The support may comprise other materials and is only to be limited as recited in the appended claims.

Without to being bound to theory, the straps, bands, or ribbons serve to more evenly distribute force loads across the lower pole support (and across multiple affixation points) so as to reduce the load and failure at any one location point. Additionally the ribbons do not garrote the tissue as sutures may do under certain circumstances. These are advantages over standard breast lift devices which use sutures to support the loads.

Additionally, in the support 500 shown in FIG. 5A, the suspension arms 510*a*, 510*b* are shown having a curvature. In particular, the arms or straps are shown being concave upwards from the vertical axis of symmetry 516. However, the curvature and shape of the arms may vary widely. The arms and leg members may be straight or curved.

Figure 5B:
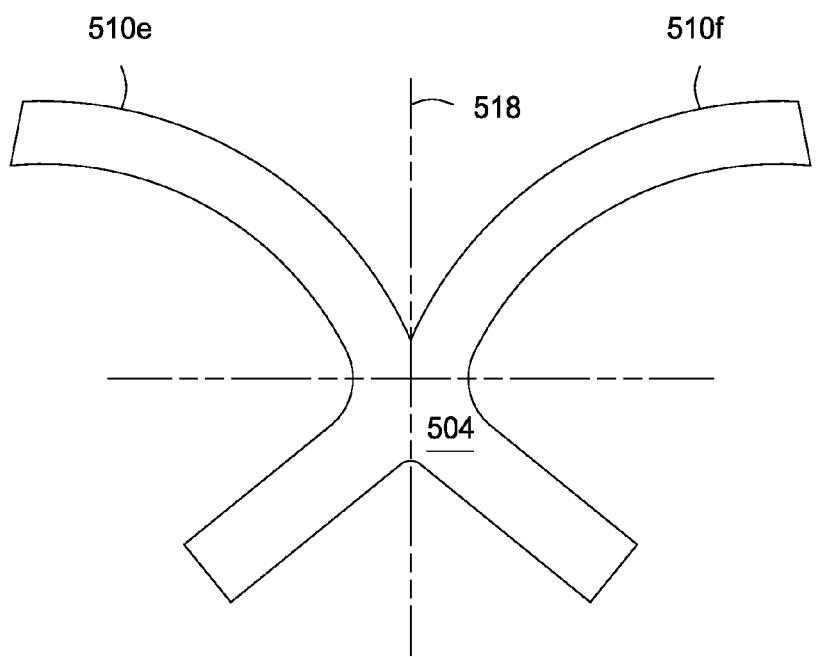

FIG. 5B shows another support 504 for lifting a breast tissue. Support 504 is shown in an undeployed or unrolled state with the environment removed for clarity. The support 504 is similar to the support 500 described above except that the arms 510 *e,f* are convex downward relative to the vertical axis of symmetry 518.

The length of the arms may vary and range from about 5 to 30 cm and preferably are about 18 cm. The length of the legs and the widths may be similar to that described above in connection with support 500 of FIG. 5a.

Figure 6A:
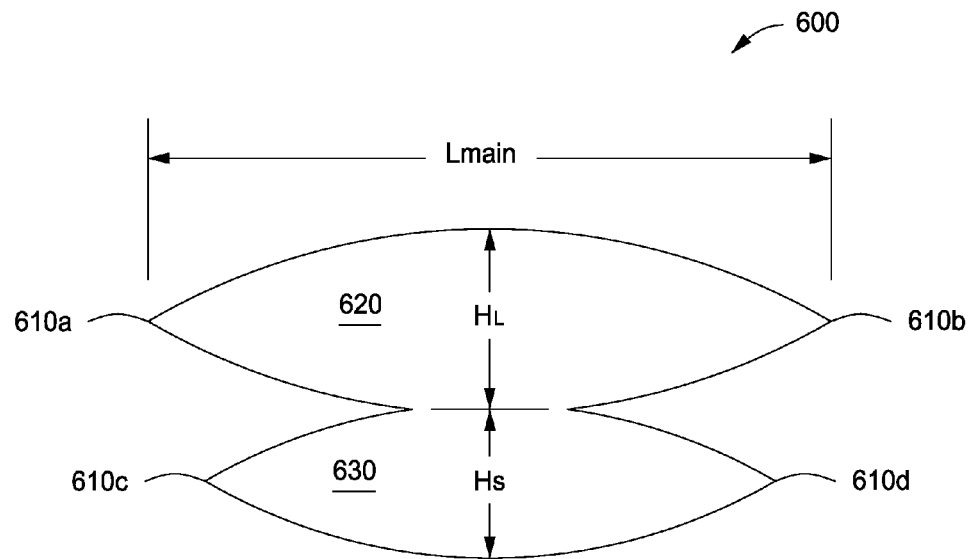
FIGS. 6A and 6B illustrate lower pole supports having elliptical shapes.

FIG. 6A illustrates another lower pole support. Support 600 includes an upper region 620 having an elliptical shape and a lower region 630 having a similar shape to the upper region, albeit a different size. The dual elliptical (or football) support 600 shown in FIG. 6A includes four ends 610*a, b, c, d*. The ends or end portions of the two ellipses may be used as anchoring points to affix the support to the chest wall or other supportive tissue as will be described in more detail below.

Figure 6B:
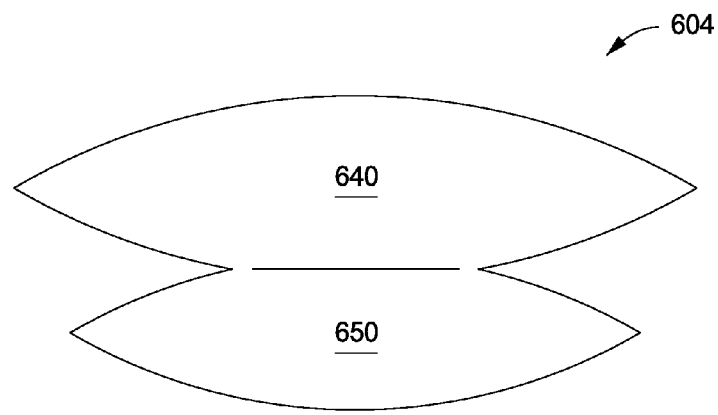

The top ellipse 620 is shown having a similar or slightly larger footprint or property than that of lower ellipse 630. However, the shapes may vary widely. The sizes may be substantially different as shown in FIG. 6B where upper ellipse 640 is much greater than lower ellipse 650. The figures are intended only as examples, and the upper footprint or property of the breast support device 600 may be larger, equal, or smaller than the lower footprint or property.

Additionally, the shapes themselves may be different or similar. For example, an upper ellipse may be stacked or otherwise combined with a lower crescent, half moon, semi-circle, rectangle, or any other shape contemplated herein. Additionally, one or more of the regions may comprise one or more straps or bands as described above in connection with FIGS. 5A-5B.

The specific dimensions of the support may vary. Exemplary non-limiting lengths (Lmain) for the larger ellipse 620 along its long or main axis ranges from 16 to 36 and perhaps about 25 cm. The larger ellipse 620 may have a height dimension (Hl) ranging from 4 to 12 and in one embodiment is about 7 cm.

The smaller ellipse 630 is preferably centered relative to the top ellipse and has a long axis ranging from 12 to 25 and perhaps about 17 cm. The smaller ellipse 630 may have a height dimension (Hs) ranging from 2 to 10 and in one embodiment is about 5 cm. Additionally, the top crescent may be approximately 2 times the width of the bottom shape.

The materials of the support shown in FIGS. 6A-6B may be similar to the materials and compositions of the mesh and supports described herein.

Figure 7A:
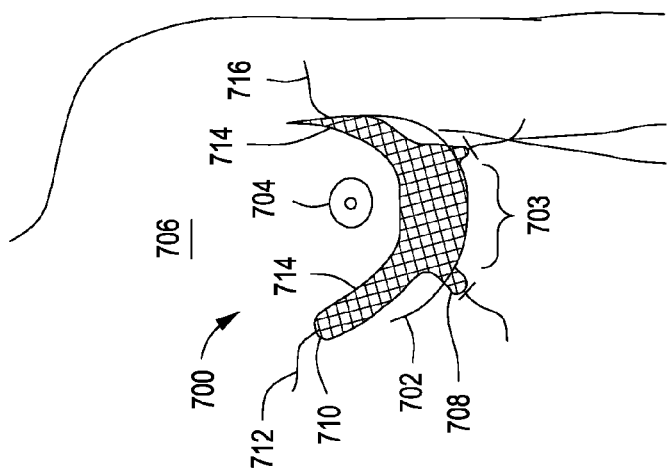
FIGS. 7A-7C illustrate schematically various lower pole supports deployed in the breast to lift the lower pole and the NAC.
Figure 7B:
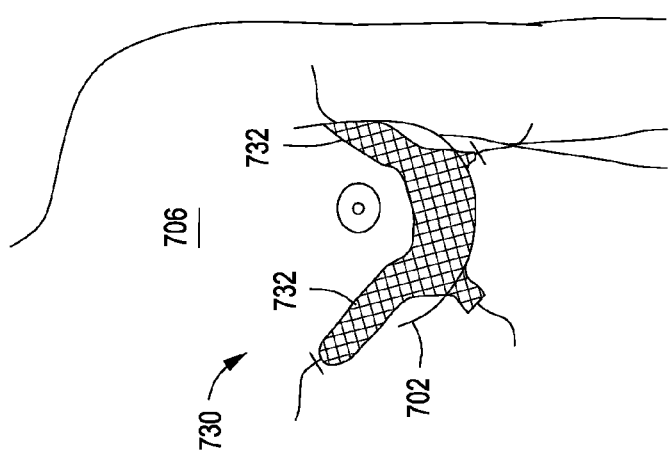
Figure 7C:
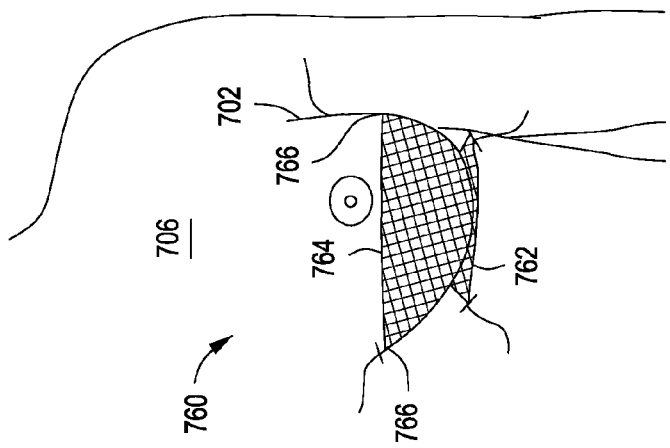

FIGS. 7A, 7B, and 7C illustrate various tissue supports 700, 730, and 760 respectively deployed in the breast 702 of a patient 706, serving to lift the lower pole of breast and the NAC 704 to a target position. The skin of the breast is not shown for clarity of illustrating the positioning and shapes of the supports. As will be discussed in more detail below, the supports are positioned through one or more incisions and into a subcutaneous pocket.

With reference to FIG. 7A, support 700 includes a central body portion 703 and four straps including two upper straps 714 and two lower straps 708 extending from the body portion. The lower straps 708 are manipulated inferiorly and affixed to supportive tissue on the chest wall. Sutures 712 may be used affix the straps to the chest wall.

Upper straps 714 are manipulated across the breast parenchyma and fixed to the chest wall at locations 716. The support 700 anchors the lower pole of the breast parenchyma in a target position.

With reference to FIG. 7B, a support 730 is shown in a deployed state and includes substantially the same features as that described in connection with the support 700 of FIG. 7A except that the upper arms members 732 are different than the upper straps 714. In particular, the upper arm members 732 shown in FIG. 7B have a convex curvature with respect to a vertical axis of symmetry. The arm members 732 curve slightly outward.

Without being bound to theory, this difference in shape in the straps is desirable in certain cases and for adjusting or designing certain shaped lifts. The convex curvature tends to place forces at a more superior location of the breast, thereby providing a different appearance or shape to the breast. Adjusting the degree of curvature can adjust the shape or lift.

With reference to FIG. 7C, support 760 is shown in a deployed state and includes a smaller elliptical region 762 fixed to the chest wall, and a larger elliptical region 764 enveloping the breast parenchyma and fixed at its end portions 766 or corners, thereby creating a sling to support the breast 702 in a lifted position.

Figure 8A:
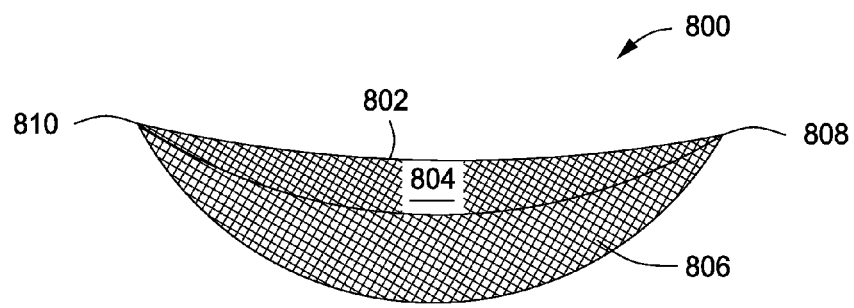
FIGS. 8A-8C illustrate various lower pole supports comprising a canoe shape.

FIG. 8A shows another support 800 having a 3D shape. In particular, the support 800 shown in FIG. 8*a* includes a canoe-like body including walls 802, 806 and a cavity 804 formed therein. The cavity 804 serves to accommodate the breast parenchyma when deployed.

An exemplary non limiting length is about 22 cm, and having a flexibility or elasticity to be extended 10% lengthwise. Exemplary, non-limiting, curvatures for the two radii shown in FIG. 8A are about 5.5 cm and 4.5 cm with extensibility of 50-100%.

The support may comprise a unitary sheet or mesh made of polymer such as that described herein which is cut and folded into the 3D shape or structure. An exemplary pore size is preferably about 1 mm.

The support 800 is affixed to the chest wall or other supportive tissue of the patient at two points to provide soft tissue support in the breast. Ends 808,810 are affixed to the patient points on the chest wall. In embodiments, a suture, hook, tack, or other anchoring mechanism may be attached to the end portions for anchoring or affixing the end portions to the supportive tissue.

Figure 8B:
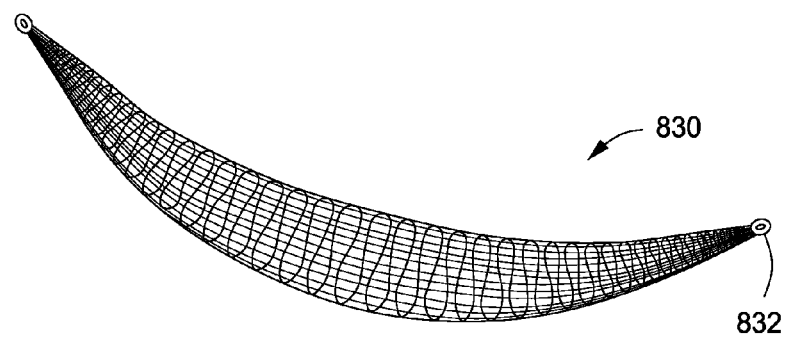
Figure 8C:
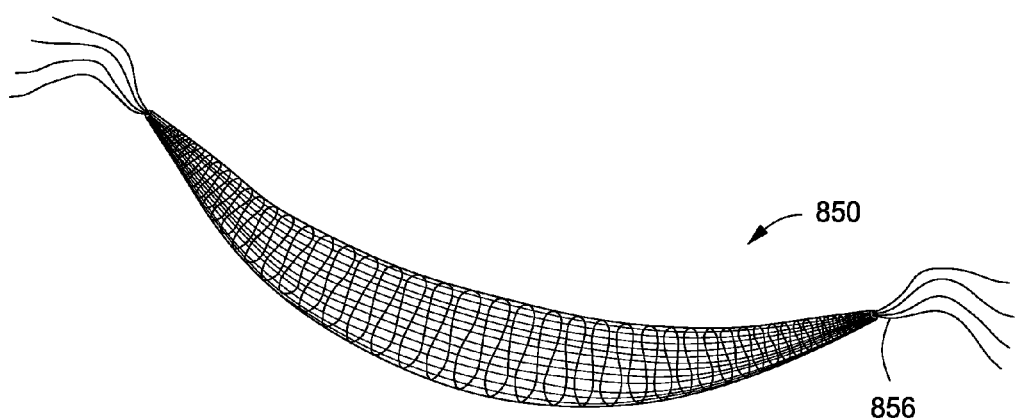

FIG. 8B illustrates, for example, a support 830 comprising rings 832 for attaching to supportive tissue or another fixture device as the case may be. FIG. 8C illustrates, for example, a support 850 comprising sutures 856 for attaching to supportive tissue or another fixture device as the case may be. However, the invention is not so limited and a wide variety of means may be incorporated to attach the ends, end portions, straps or supports to the supportive tissue. Also, by "supportive tissue" it is meant to include without limitation tissue of chest wall including subglandular, fascial, bony, cartilaginous, and muscular tissues.

Upon attachment to the supportive tissue and/or to a suspension strut as described above, the lower pole support is positioned to provide sufficient elevating force to the breast to relieve the prediagnosed ptosis in such a manner as to also relieve force on the incision sites and skin of the lower pole. In an embodiment, the lower pole support can be temporarily affixed to the supportive tissue and/or suspension strut, with the tension on the system being adjusted intraoperatively. It may be desirable to adjust the patient's position to a sitting or upright position to optimize the tension on the system and the subsequent correction of the breast ptosis.

The lower pole support (e.g., without limitation support 413, 500, 600, 700, 800, etc.) can be configured as a sheet, a solid sheet, or as a discontinuous layer such as a mesh. Non-limiting examples of a support include a mesh, a set of strips, a fabric, a woven construct, a knitted construct, a braided construct, a porous scaffold, a nanospun, electrospun, or melt-blown construct.

In embodiments, the lower pole support can be made from the same materials (e.g., the biodegradable polymeric materials) described as usable for the suspension strut. Suitable tissue derived products include allograft, autograft, xenograft, collagen, and the like. Also included are compositions in which two or more naturally derived and synthetic materials are used to form a composite structure to impart optimal resorption characteristics and strength retention.

In embodiments, the lower pole support can comprise biocompatible metals. In embodiments, the lower pole support can be made from a composite of materials described above.

In embodiments, the lower pole support can comprise biodegradable and/or resorbable materials. Preferably, such a material would be selected so that it provides adequate tensile strength to support the breast and lengthen the time over which the corrected lift remains stable, and so that the corrected position is stabilized by the formation of a layer of collagen or scar tissue concomitant with the lower pole support losing strength.

Preferred materials include poly-4-hydroxybutyrate and polydioxanone, silk-based fibers and other biodegradable polymers. Other materials that may be suitable if structured appropriately include allograft or xenograft materials or biodegradable polymers with shorter strength retention times. Similarly, the preferred materials for the suspension strut are biodegradable materials with long strength retention times as described above. In embodiments, the components of the mastopexy system disclosed herein are substantially biodegradable and/or resorbable, so that a durable breast lift can be provided without leaving permanent foreign bodies in the breast region. Such a biodegradable/resorbable system would provide sufficient and long-lasting tensile strength to allow the repositioned breast tissues to remain in place while tissue remodeling and collagen deposition around the resorbing implant occurs, with the long-term lifted shape of the breast being maintained by newly generated durable fibrous tissue.

Mastopexy Procedure

FIGS. 9A-9F illustrate steps of a mastopexy procedure. In particular, FIGS. 9A-9F show installation of tissue support 900 into a breast. The support lifts the lower pole of the breast from a first position 902' to a target position 902".

Figure 9C:
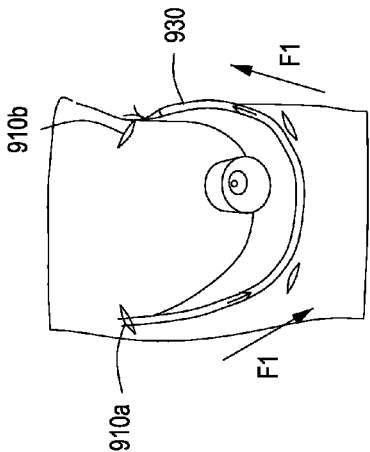
FIGS. 9A-9F illustrate schematically a procedure for lifting the lower pole and the NAC.

Initially, and with reference to FIG. 9A, one or more upper incisions 910 a,b are created at the lateral and medial portions of the breast and lower incisions 910c,d are created proximal to the inframammary fold, slightly below the lower border of the NAC 912. Additionally, a crescent shaped portion of skin 908 is removed from above the NAC 912.

Figure 9B:
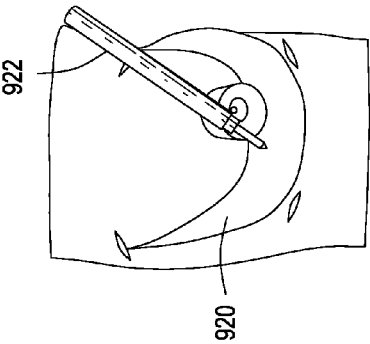
Figure 9A:
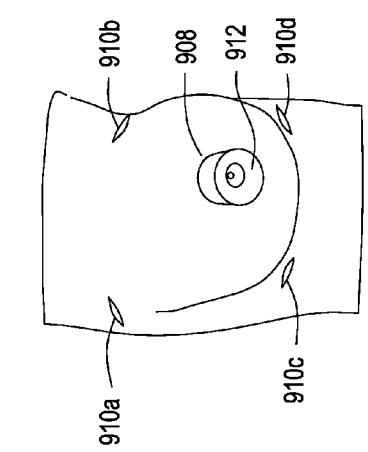

FIG. 9B illustrates a step of creating a subcutaneous pocket 920 using a dissector tool 922 inserted through the NAC incision. Dissection is performed to create a preferably triangular shaped pocket in the superficial, inferior half of the breast, with one side of the triangle lying tangent to the inferior-most portion of the NAC 912. The pocket 920 serves to accommodate support 900.

In embodiments, the pocket may be defined or characterized as comprising a number of regions including a frontal or more anteriorly-disposed main region as well as a plurality deep regions extending to points on, or in close vicinity to, the chest wall. In embodiments, two deeper regions or pockets are created superior to the NAC in the same subcutaneous plane as the main region for placement of upper straps 904. Similarly, in embodiments, two deeper regions or pockets are preferably created inferior to the NAC for placement of lower straps 906.

FIG. 9C illustrates advancing an insertion device 930 into the subcutaneous pocket at the lateral incision 910a and fed along the side of the pocket tangent to the NAC, to the medial incision 910b. The direction is indicated by reference numeral F1 in FIG. 9c. The insertion device is preloaded with the lower pole support 900. The lower pole support 900 depicted in FIGS. 9a-9f includes four suspension arms (each arm being pre-strung with two lines of suture, and one suture at the end of each superior "arm"). The lower pole support is folded (preferably in half) and then rolled up and placed into the insertion device. The suture lines 940 may protrude out of the distal end of the insertion device.

Figure 9F:
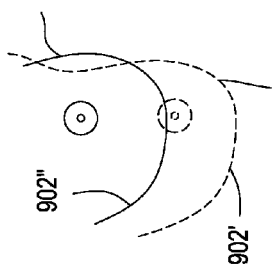
Figure 9E:
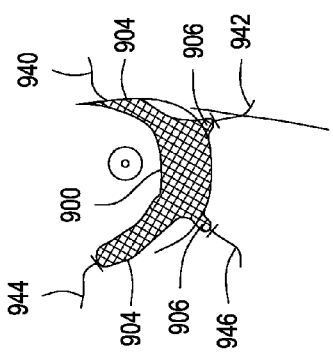
Figure 9D:
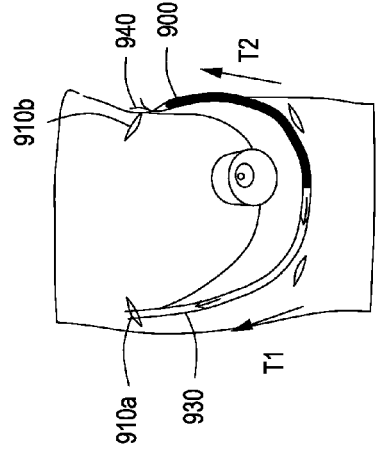

FIG. 9D illustrates deploying the lower pole support 900. Deployment may be carried out by retracting the insertion device 930 with a force T1 while grasping suture lines 940 and applying a tension or force to the sutures 940 in the direction indicated by T2. The insertion device 930 is removed horizontally, deploying the lower pole support 900 into the subcutaneous pocket 920.

FIG. 9E illustrates manipulating or positioning the lower pole support. In particular, by holding the lines of suture, the straps 904, 906 can be manipulated to optimize the placement of the lower pole straps. The option of sitting the patient up to better align the breast placement is also available. The straps are placed through the deep pockets. If desired, additional small incisions may be made to provide improved access for manipulation of the support.

FIG. 9f illustrates the breast lifted from a first position 902' to the target position 902". The breast may be manipulated from the first position to the target position by adjusting the breast directly by hand or manipulating the straps or portions of the lower pole support. Once the breast is in the target position, the straps are affixed. Examples of affixation techniques are described above and include, for example, tacking the straps to the supportive tissue, suturing the straps to the supportive tissue, or attaching the straps to anchors fixed to the supportive tissue.

In some embodiments, a periareolar incision can also be used to properly place the support inferiorly around the lower pole of the breast parenchyma. An inframammary incision is made and wire subscision may be used to expand the inferior point of the triangle pocket, so that the pocket is more square shaped. Additionally, wire subscision or electrocautery may be used again to dissect deep to the breast, to two points on the chest wall that are inferior and medial to the initial two fixation points. Absorbable tacks may be used to fix the "legs" of the support to the same plane of the chest wall where the "arm" fixation exists.

Although the method described above in connection with FIGS. 9a-9f describes implanting one type of lower pole support, it is to be understood that the invention is not so limited. And other types of lower pole supports may be implanted in methods of the present invention.

Additionally, the step of dissecting may be performed variously including without limitation blunt dissection, electrocautery, or wire subscision.

Electrocautery or blunt dissection may be carried out through the various incisions described above. The instrument is inserted through the incision and the pocket is created by applying force or energy or a combination of both.

Figure 10C:
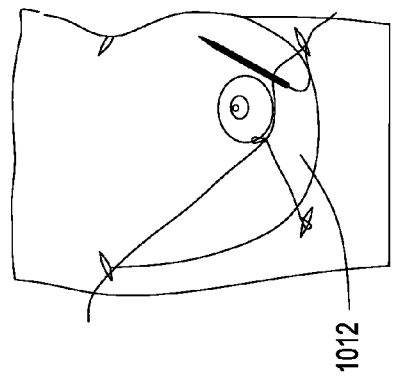
FIGS. 10A-10E illustrate schematically a procedure for creating a subcutaneous pocket for accommodating a lower pole support.
Figure 10B:
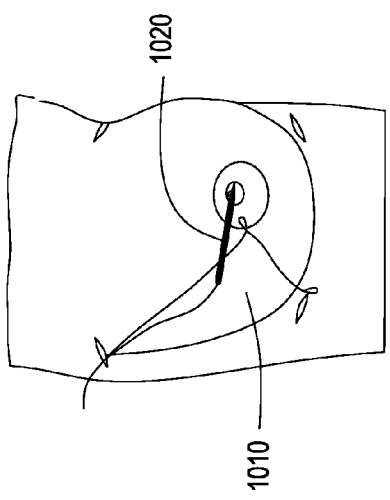
Figure 10A:
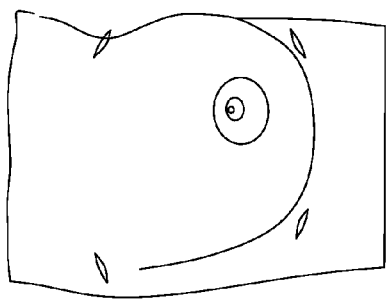
Figure 10E:
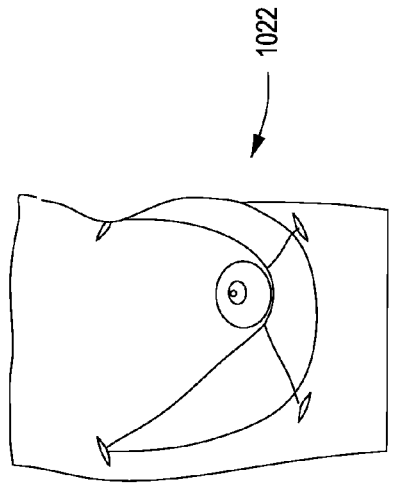
Figure 10D:
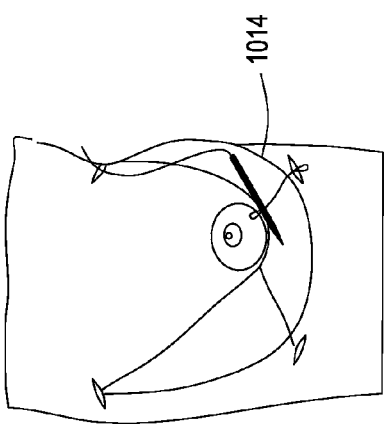

An example of wire subscision is illustrated in FIGS. 10a-10e. With reference to FIG. 10a, a plurality of incisions are made as described above. Preferably two medial and two lateral incisions are made. Next, as illustrated in FIGS. 10b-10d, a plurality of contiguous pockets 1010, 1012, 1014 are created. Preferably the pockets are triangular shaped, and sequentially formed with a needle wire member 1020. The needle is manipulated from under the skin to form a subcutaneous triangular shaped pocket and then withdrawn, thereby separating the skin from the tissue to form the respective pocket.

FIG. 10e illustrates an example of a contiguous triangular shaped pocket 1022 for accommodating various lower pole supports described above.

EQUIVALENTS

While specific embodiments of the subject invention have been discussed, the above specification is illustrative and not restrictive. Many variations of the invention will become apparent to those skilled in the art upon review of this specification. Unless otherwise indicated, all numbers expressing quantities or properties of components or methods used in the specification and claims are to be understood as being modified in all instances by the term "about." Accordingly, unless indicated to the contrary, the numerical parameters set forth herein are approximations that can vary depending upon the desired properties sought to be obtained by the present invention.

While this invention has been particularly shown and described with references to preferred embodiments thereof, it will be understood by those skilled in the art that various changes in form and details may be made therein without departing from the scope of the invention encompassed by the appended claims.

The invention claimed is:

1. An implant for securing a breast of a patient in a lifted position, the implant comprising:
    a lower pole support comprising a body having a low-profile configuration, and a self-deploying 3D pre-determined configuration larger than the low-profile configuration, and wherein said 3D pre-determined configuration is sized such that the body substantially spans a lower pole of the breast when deployed; and
    a plurality of flexible strap members extending in the upwards direction and lower direction from the body, and wherein said plurality of flexible strap members are integrally formed with said body, wherein the body comprises a material that maintains the 3D pre-determined configuration when unconstrained.

2. The implant of claim 1 wherein the body is a composite of different materials.

3. The implant of claim 2 wherein each of the materials of the body is biodegradable.

4. The implant of claim 3 wherein the body comprises a polymer.

5. The implant of claim 4 wherein the body comprises a porous structure.

6. The implant of claim 1 wherein the body has a canoe-like shape.

7. The implant of claim 1 wherein the body has radius of 4.5 or 5.5 cm.

8. The implant of claim 1 wherein the body has a length of 22 cm.

9. The implant of claim 1 wherein each of the straps has a width between 0.25 to 5 cm.

10. The implant of claim 1 further comprising a plurality of sutures extending through said straps and for securing the straps to supportive tissue, causing the breast to be secured in the lifted position.

11. The implant of claim 1 wherein the plurality of flexible straps comprises more than five straps including at least two upper straps and two lower straps.

12. The implant of claim 1 wherein the body and straps comprises a silk-based material.

13. The implant of claim 1 wherein the body and straps comprises poly-4-hydroxybutyrate (P4HB).

14. The implant of claim 1 wherein at least one of the straps extends in a lateral direction.

15. The implant of claim 1 wherein the straps are extendable.

16. The implant of claim 15 wherein the straps are extendable up to 10%.

17. An implant for securing a breast of a patient in a lifted position, the implant comprising:
    a lower pole support comprising a body having a low-profile configuration, and a self-deploying 3D pre-determined configuration larger than the low-profile configuration, and wherein said 3D pre-determined configuration is sized such that the body substantially spans a lower pole of the breast when deployed; and
    a plurality of flexible bands extending in the upwards direction and lower direction from the body, and wherein said plurality of flexible bands are integrally formed with said body, wherein the body is comprises of a shape-memory material to provide the 3D pre-determined configuration.

18. The implant of claim 17 wherein the body comprises a canoe-like shape.

19. The implant of claim 17 wherein the plurality of flexible bands comprises more than five bands.

20. The implant of claim 17 wherein the implant is flexible and capable of being rolled cylindrically prior to being deployed.

21. An implant for securing a breast of a patient in a lifted position, the implant comprising:
    a lower pole support comprising a body having a low-profile configuration, and a self-deploying 3D pre-determined configuration larger than the low-profile configuration, and wherein said 3D pre-determined configuration is sized such that the body substantially spans a lower pole of the breast when deployed; and wherein the body further comprises a mesh, sheet, fabric, woven construct, knitted construct, braided construct, porous scaffold, nanospun, electrospun, melt-blown construct; and
    a plurality of flexible strap members extending in the upwards direction and lower direction from the body, and wherein said plurality of flexible strap members are integrally formed with said body.

22. The implant of claim 1 wherein the low-profile configuration comprises the body in a rolled state.

23. The implant of claim 17 wherein the low-profile configuration comprises the body in a rolled state.

* * * * *

UNITED STATES PATENT AND TRADEMARK OFFICE
CERTIFICATE OF CORRECTION

PATENT NO. : 9,585,744 B2  
APPLICATION NO. : 14/830685  
DATED : March 7, 2017  
INVENTOR(S) : Arikha Moses et al.

Page 1 of 1

It is certified that error appears in the above-identified patent and that said Letters Patent is hereby corrected as shown below:

In the Claims

Claim 7, Line 1, the text "has radius" should read "has a radius".

Claim 17, Lines 12-13, the text "wherein the body is comprises of a shape-memory material" should read "wherein the body comprises a shape-memory material".

Column 9, Lines 33-34, the term "enymatic" should read "enzymatic".

Column 10, Line 33, the term "poly4-hydroxybutyrates" should read "poly-4-hydroxybutyrate".

Signed and Sealed this  
Twenty-seventh Day of June, 2017

Joseph Matal  
*Performing the Functions and Duties of the*  
*Under Secretary of Commerce for Intellectual Property and*  
*Director of the United States Patent and Trademark Office*